(12) United States Patent
Yamamura et al.

(10) Patent No.: US 9,572,543 B2
(45) Date of Patent: Feb. 21, 2017

(54) TOMOGRAPHY SYSTEM

(71) Applicant: Konica Minolta, Inc., Chiyoda-ku, Tokyo (JP)

(72) Inventors: Takuya Yamamura, Hachioji (JP); Youichi Ono, Akiruno (JP); Koutarou Kanamori, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 233 days.

(21) Appl. No.: 14/573,255

(22) Filed: Dec. 17, 2014

(65) Prior Publication Data

US 2015/0164455 A1 Jun. 18, 2015

(30) Foreign Application Priority Data

Dec. 18, 2013 (JP) ................................. 2013-260756

(51) Int. Cl.
*A61B 6/00* (2006.01)
*A61B 6/02* (2006.01)
*A61B 6/03* (2006.01)

(52) U.S. Cl.
CPC ............. *A61B 6/5258* (2013.01); *A61B 6/025* (2013.01); *A61B 6/032* (2013.01); *A61B 6/5205* (2013.01); *A61B 6/585* (2013.01)

(58) Field of Classification Search
CPC ............. A61B 6/00; A61B 6/02; A61B 6/025; A61B 6/04; A61B 6/5258; G01N 23/02; G01N 23/04; G01N 23/046; G01N 23/08; G01N 23/083
USPC ................ 378/21, 23, 25, 26, 167, 207, 901
See application file for complete search history.

(56) References Cited

FOREIGN PATENT DOCUMENTS

| JP | 2011-36407 A | 2/2011 |
|---|---|---|
| JP | 2013-55971 A | 3/2013 |

*Primary Examiner* — Jurie Yun
(74) *Attorney, Agent, or Firm* — Cantor Colburn LLP

(57) ABSTRACT

A tomography system includes a radiation source, a radiation detector, a subject table, an imaging unit and a reconstruction unit. The imaging unit obtains a projection image a predetermined number of times while changing a positional relationship of the radiation source and the radiation detector. The reconstruction unit generates a tomogram of a subject using the projection image obtained by the imaging unit. The reconstruction unit includes a correction unit. The correction unit performs correction processing to (i) create a profile of a pixel signal value from a no-subject-included projection image obtained by the imaging unit without the subject on the subject table and (ii) correct, on the basis of the created profile, a subject-included projection image obtained by the imaging unit with the subject on the subject table or a detection probability used in generating the tomogram.

12 Claims, 10 Drawing Sheets

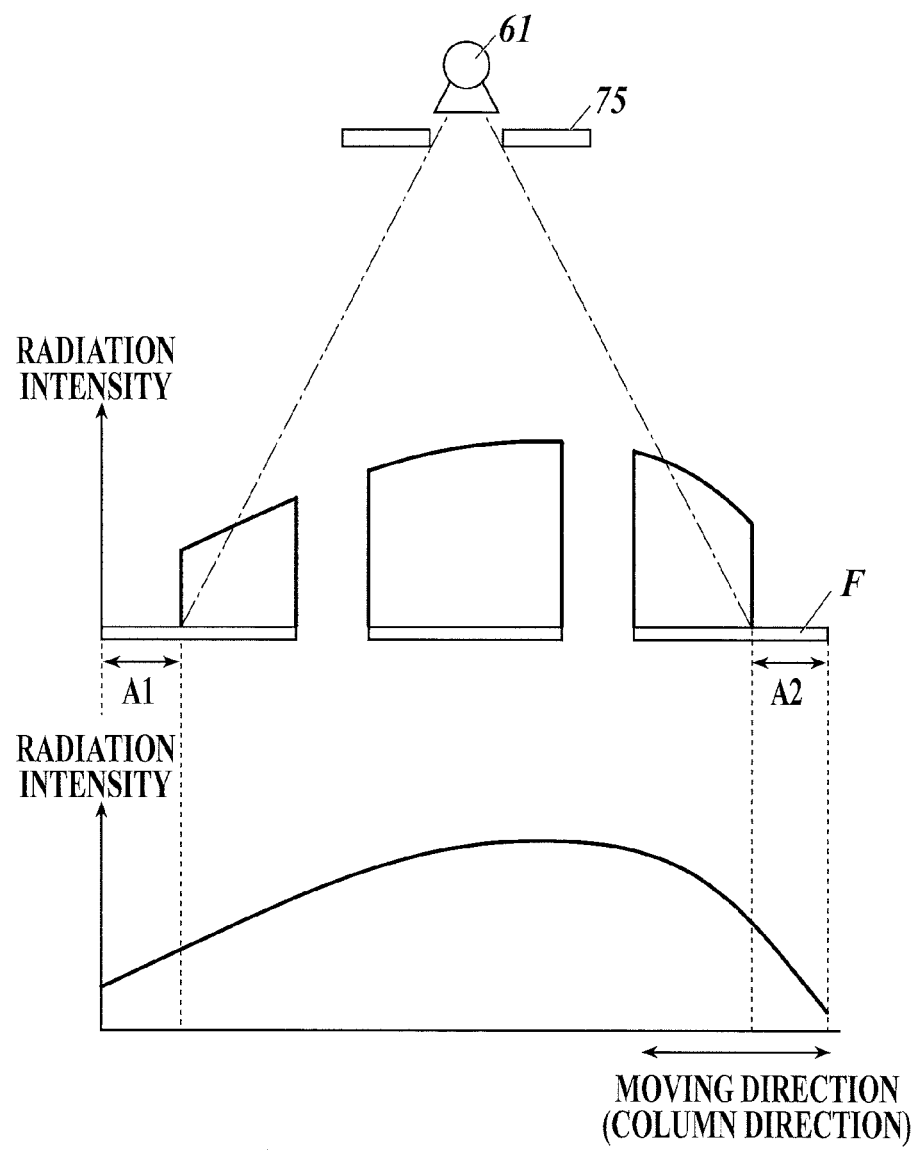

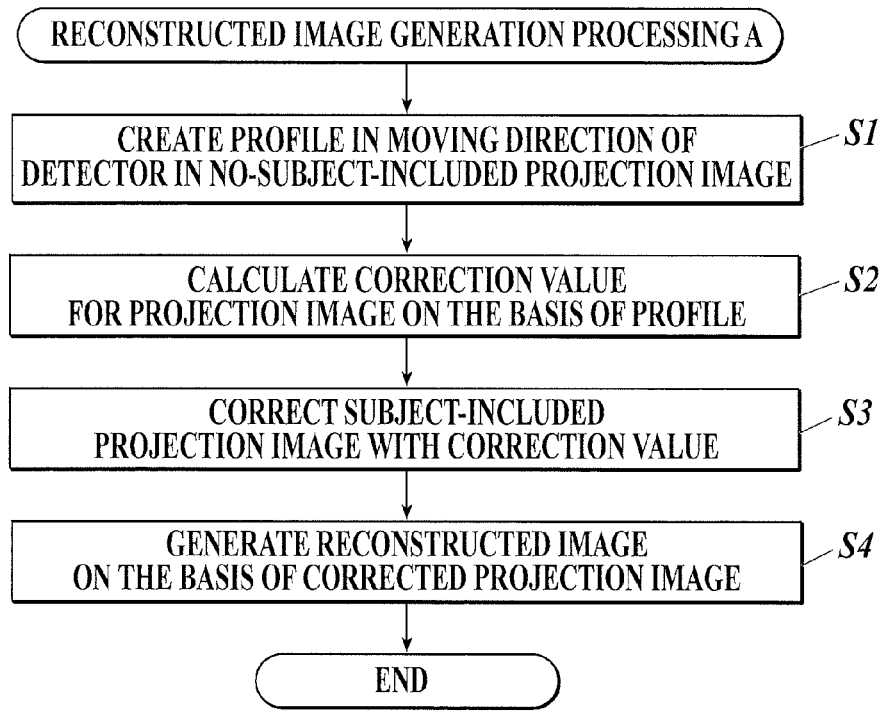
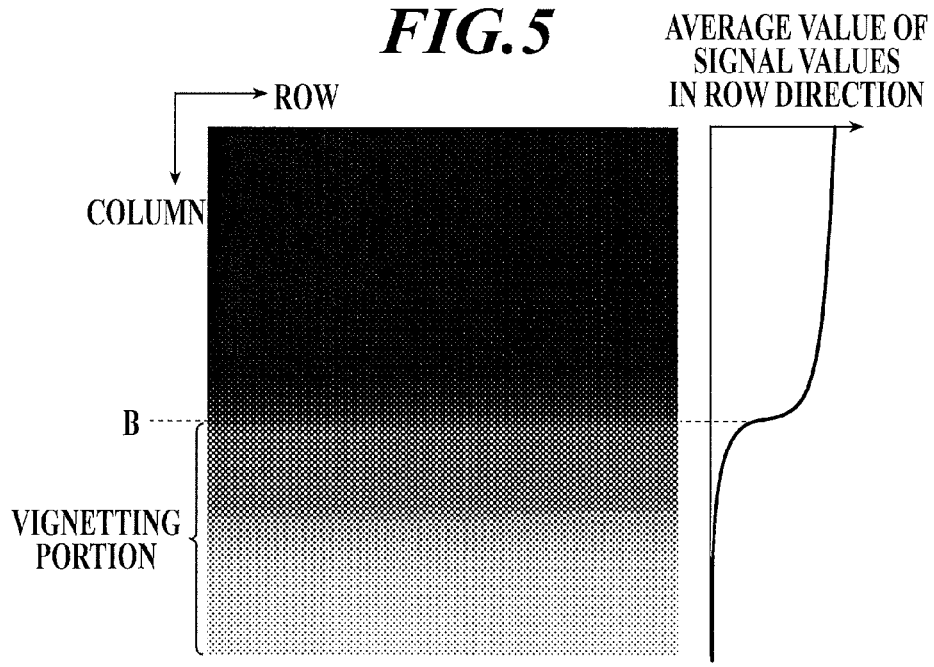

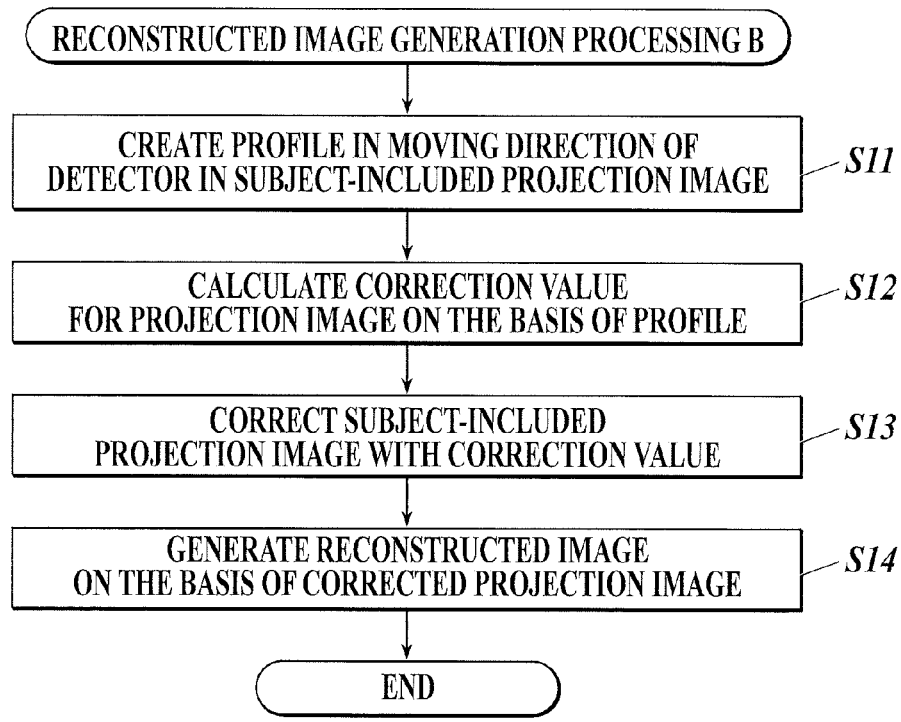
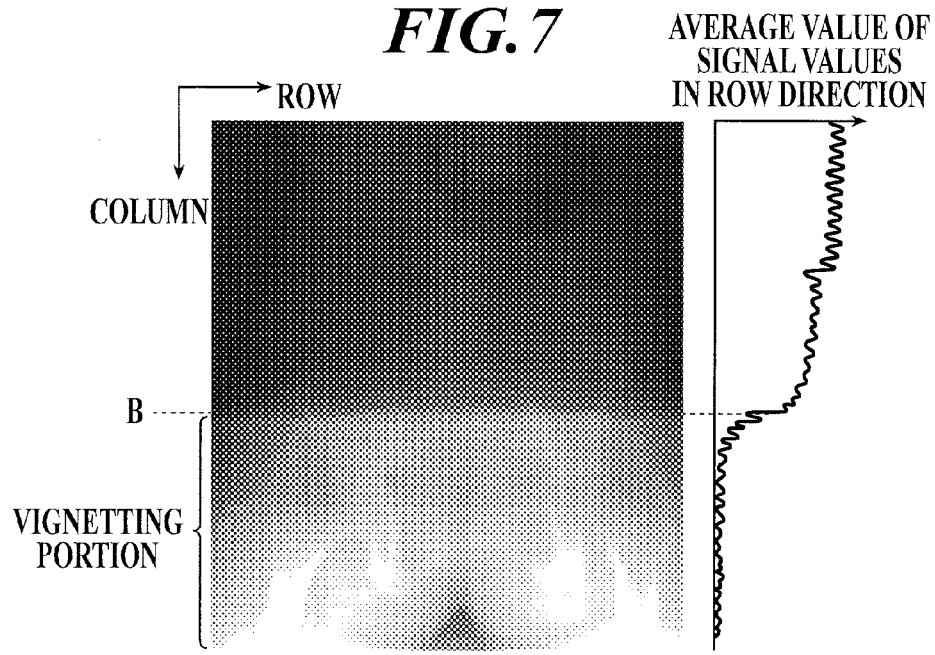

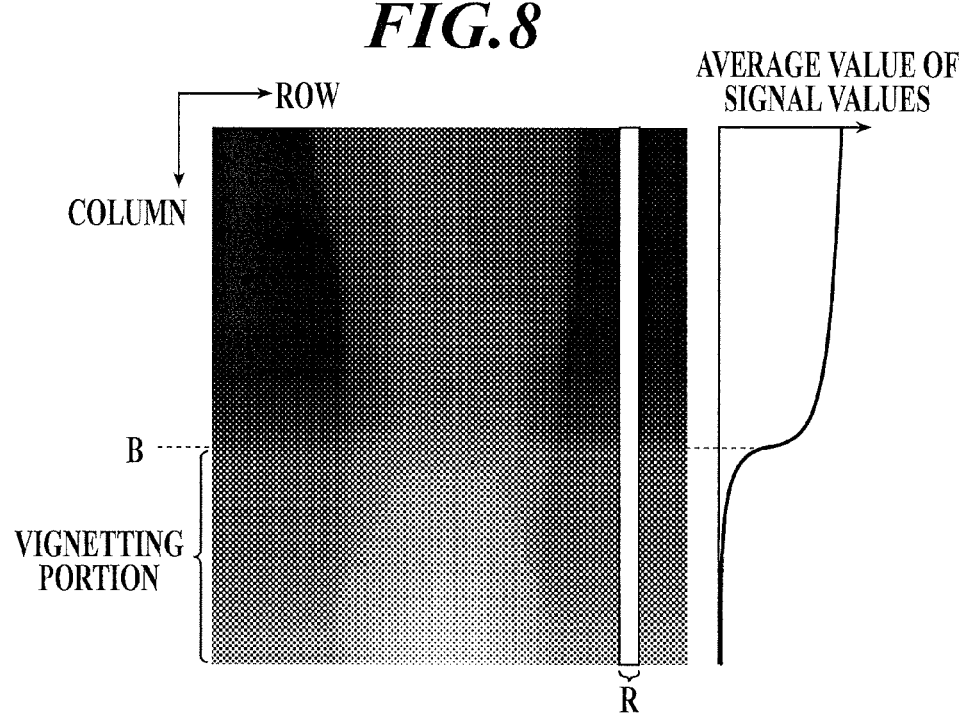

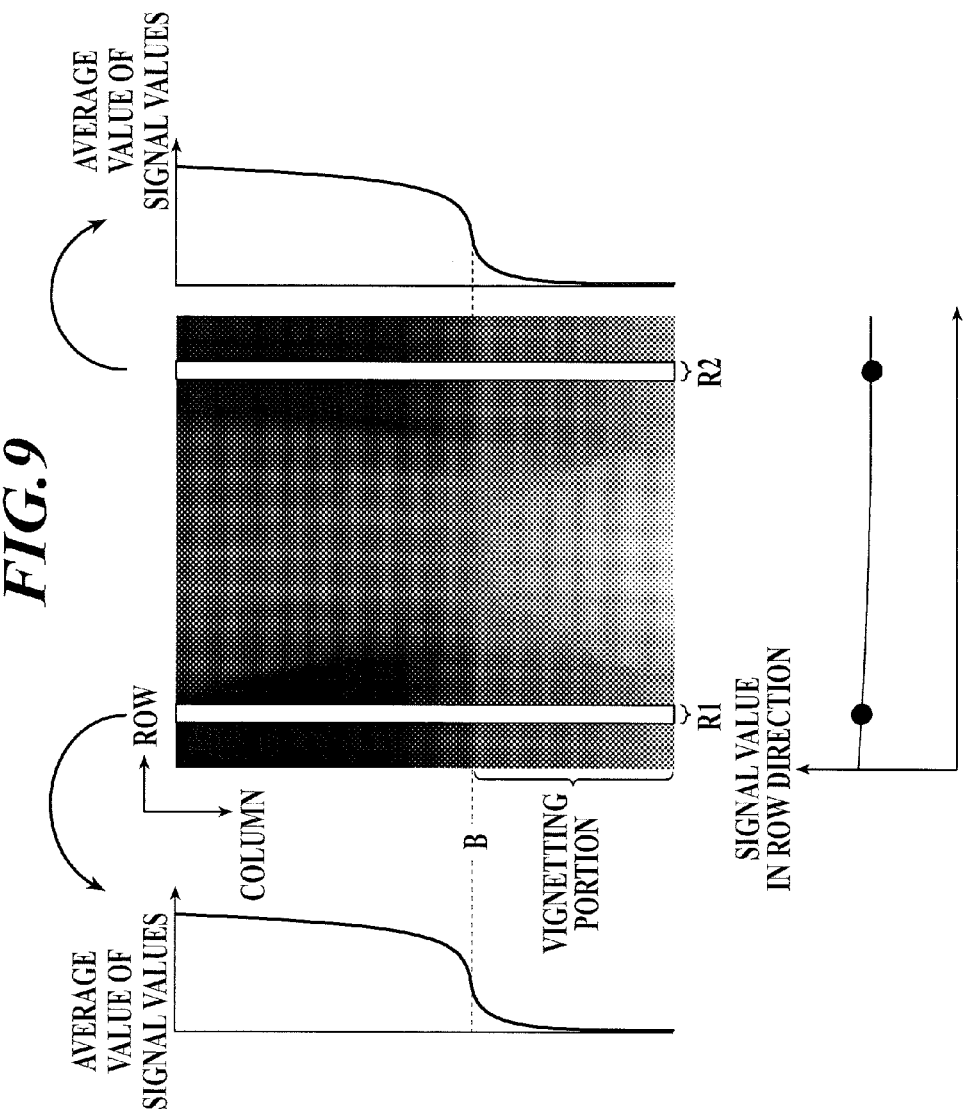

TOMOGRAPHY SYSTEM

CROSS REFERENCE TO PRIOR ART

The present invention claims priority under 35 U.S.C. §119 to Japanese Application No. 2013-260756 filed Dec. 18, 2013, the entire content of which is incorporated herein by reference.

FIELD OF THE INVENTION

The present invention relates to a tomography system.

DESCRIPTION OF THE RELATED ART

In recent years, there has been used in the field of medical services a tomography device which performs tomosynthesis imaging, thereby emitting radiation to the body of a patient as a subject from around the body, converting the radiation having passing through the subject into electric signals and obtaining the electric signals as projection images. An image processing device performs reconstruction using the projection images of the subject obtained by the tomography device, thereby generating two-dimensional tomograms at predetermined cross sections of the subject.

However, in the tomograms obtained by reconstruction using the projection images obtained by tomosynthesis imaging, various artifacts appear. Hence, there have been proposed various arts to avoid this happening.

There is described, for example, in Patent Document 1 (Japanese Patent Application Laid-Open Publication No. 2011-36407) correcting a luminescence correction coefficient according to the number of superimposed perspective images (projection images) at each point in a tomogram region in order to reduce luminescence non-uniformity caused by the number of superimposed perspective images being different at each point in the tomogram region.

Further, there is described, for example, in Patent Document 2 (Japanese Patent Application Laid-Open Publication No. 2013-55971) performing, on obtained projection data, extrapolating processing along a predetermined direction and smoothing processing along a direction perpendicular to the predetermined direction, thereby generating projection data in non-detecting regions, which do not belong to a detecting region of a radiation detector.

The art described in Patent Document 1 is, however, applicable to only the case where a method for generating tomograms is the Feldkamp method and inapplicable to the case where the method therefor is another method such as the successive approximation image reconstruction method. Further, the art described in Patent Document 2 is applicable to any of these methods but cannot deal with the case where density non-uniformity (luminescence non-uniformity) exists in the detecting region of the radiation detector in a projection image(s). In addition, the art described in Patent Document 2 expands an expressible region by the extrapolating processing on the projection data, which lacks accuracy.

BRIEF SUMMARY OF THE INVENTION

Objects of the present invention include to minimize artifacts which appear in a tomogram when any of projection images obtained by imaging has density non-uniformity.

In order to achieve at least the above object, according to a first aspect of the present invention, there is provided a tomography system including: a radiation source which emits radiation to a subject; a radiation detector (i) in which radiation detection elements are two-dimensionally disposed, the radiation detection elements detecting the radiation to generate electric signals, and (ii) which obtains a projection image according to the radiation; a subject table which is disposed between the radiation source and the radiation detector and supports the subject; an imaging unit which obtains the projection image a predetermined number of times while changing a positional relationship of the radiation source and the radiation detector; and a reconstruction unit which generates a tomogram of the subject using the projection image obtained by the imaging unit, the reconstruction unit including: a correction unit which performs correction processing to (i) create a profile of a pixel signal value from a no-subject-included projection image obtained by the imaging unit without the subject on the subject table and (ii) correct, on the basis of the created profile, a subject-included projection image obtained by the imaging unit with the subject on the subject table or a detection probability used in generating the tomogram of the subject.

According to a second aspect of the present invention, there is provided a tomography system including: a radiation source which emits radiation to a subject; a radiation detector (i) in which radiation detection elements are two-dimensionally disposed, the radiation detection elements detecting the radiation to generate electric signals, and (ii) which obtains a projection image according to the radiation; a subject table which is disposed between the radiation source and the radiation detector and supports the subject; an imaging unit which obtains the projection image a predetermined number of times while changing a positional relationship of the radiation source and the radiation detector; and a reconstruction unit which generates a tomogram of the subject using the projection image obtained by the imaging unit, the reconstruction unit including: a correction unit which performs correction processing to (i) create a profile of a pixel signal value from a subject-included projection image obtained by the imaging unit with the subject on the subject table and (ii) correct, on the basis of the created profile, the subject-included projection image or a detection probability used in generating the tomogram of the subject.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein:

FIG. 3 shows distribution of intensities of radiation emitted from a radiation source and distribution of intensities of the radiation reaching each point in a moving direction of a radiation detector;

FIG. 4 is a flowchart of reconstructed image generation processing A performed by a control unit shown in FIG. 2 in a first embodiment;

FIG. 5 shows a no-subject-included projection image and a profile in the moving direction (column direction) of the radiation detector in the no-subject-included projection image;

FIG. 6 is a flowchart of reconstructed image generation processing B performed by the control unit shown in FIG. 2 in a second embodiment;

FIG. 7 shows a subject-included projection image with a subject all over the image and a profile in the moving direction (column direction) of the radiation detector in the subject-included projection image;

FIG. 8 shows a subject-included projection image having a direct exposure portion and a profile of the direct exposure portion in the moving direction (column direction) of the radiation detector in the subject-included projection image;

FIG. 9 shows a subject-included projection image having direct exposure portions on both sides and profiles of the direct exposure portions in the moving direction (column direction) of the radiation detector in the subject-included projection image;

DETAILED DESCRIPTION OF THE INVENTION

Hereinafter, preferred embodiments of the present invention are described in detail with reference to the attached drawings. However, the present invention is not limited to the illustrated examples.

First Embodiment

Configuration of Tomography System 100

Figure 1:
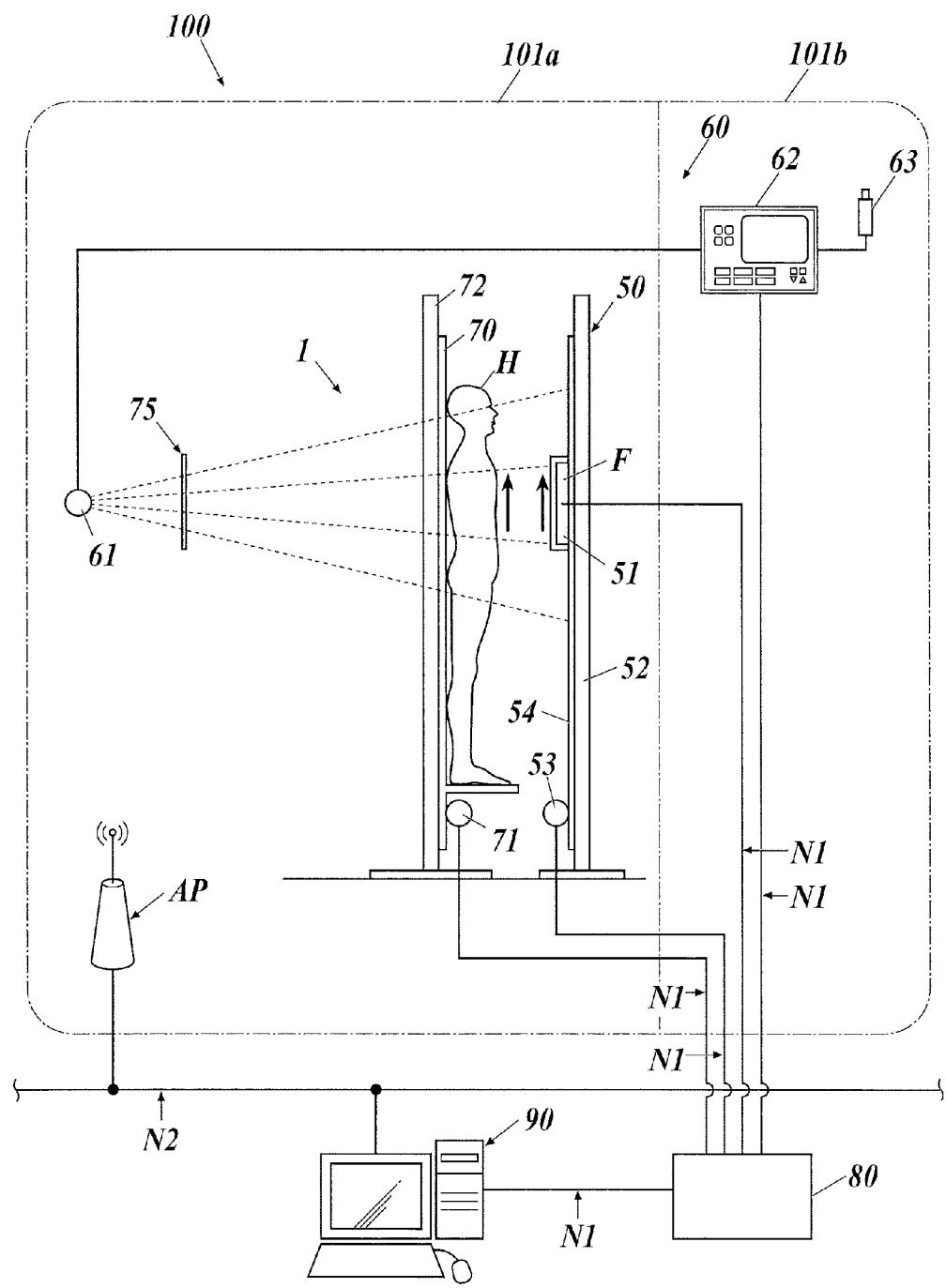
FIG. 1 shows the overall configuration of a tomography system according to embodiments of the present invention.

First, a schematic configuration of a tomography system according to a first embodiment of the present invention is described. A tomography system 100 is a system to generate each diagnostic tomogram with projection images obtained with tomosynthesis imaging of a subject H (a site of a human body). FIG. 1 shows a schematic configuration of the tomography system 100 according to the embodiment. As shown in FIG. 1, the tomography system 100 is mainly constituted of: a tomography device 1 including a radiation detector F; and a console 90.

The tomography system 100 is provided inside and outside an imaging room 101a and a front room (also called an operation room or the like) 101b. In the imaging room 101a, an imaging table 50, a radiation source 61 and the like of the tomography device 1 are disposed. In the imaging room 101a, an access point AP to rely wireless communication between the radiation detector F and the console 90 described below, and the like are also disposed.

In the front room 101b, an operator console 62, an irradiation switch 63 and the like of an irradiation device 60 are disposed. Although FIG. 1 shows that a control box 80, the console 90 and the like are disposed outside the front room 101b, they may be disposed inside the front room 101b or the like.

The tomography device 1 as an imaging unit includes, as shown in FIG. 1, the radiation detector F, the imaging table 50 which supports the radiation detector F, the irradiation device 60 and a subject table 70 which supports the subject H. FIG. 1 is a side view of the tomography device 1 which images the subject H standing as an example.

The radiation detector F is constituted of a semiconductor image sensor such as an FPD (Flat Panel Detector). The FPD has: for example, a glass substrate; and a plurality of detection elements (pixels) which are arranged at predetermined points on the substrate in a matrix. The detection elements detect radiation (X-ray) emitted from the radiation source 61 and passing through at least the subject H according to the intensity of the radiation, and convert the detected radiation into electric signals and accumulate the signals therein. Each pixel includes a switching part such as a TFT (Thin Film Transistor). The switching parts switch the pixels from which the accumulated electric signals are read, so that the electric signals accumulated in the radiation detector F are read. Thus, projection images of the subject H (subject-included projection images) are obtained. There are an indirect conversion FPD and a direct conversion FPD. In the indirect conversion FPD, radiation is converted into electric signals through a scintillator with photoelectric conversion elements. In the direct conversion FPD, radiation is directly converted into electric signals. Either type of FPD can be used.

Values (signal values) of pixels of a projection image are values of intensities of radiation which is emitted from the radiation source 61 and reaches the radiation detector F converted into electric signals, namely, values relative to the intensities of the radiation which reaches the radiation detector F. The higher the intensity of the reached radiation is, the larger the signal value is. In the embodiment, the larger the signal value of a projection image is, the blacker (at the higher density) the pixel is depicted.

The radiation detector F has: a function to communicate with the console 90 via a network N1 and the control box 80; and a wireless communication function to communicate with the console 90 via the access point AP.

The imaging table 50 includes a fitting part 51 which supports the radiation detector F, a support part 52, a carry device 53 and a fitting-part support part 54. The imaging table 50 is disposed in such a way that a radiation incidence face of the radiation detector F faces the subject H supported by the subject table 70. The imaging table 50 is configured in such a way that the fitting-part support part 54 moves (goes up and down) with the carry device 53 in synchronization with the subject table 70 in relation to the radiation source 61 according to an instruction from the control box 80, whereby the radiation detector F and the subject H can move in the same direction at the same speed.

The irradiation device 60 includes the fixed radiation source 61 which irradiates the radiation detector F through the subject H, the operator console 62 with which a photographer such as a radiologist can set a tube current, a tube voltage, an irradiation time and the like, and the irradiation switch 63 which the photographer operates to make an instruction to emit radiation from the radiation source 61. In an irradiation direction of the radiation source 61, a collimator 75 is provided. The collimator 75 limits an irradiation area of the radiation emitted from the radiation source 61.

In the embodiment, as the radiation source 61 of the irradiation device 60, a radiation source which conically emits radiation to the subject H and the radiation detector F, namely, a radiation source which emits, what is called, cone beams, is used. Alternatively, a radiation source which emits radiation spreading in the shape of an approximate plane taking the radiation source as its fulcrum (i.e. a fan shape), namely, a radiation source which emits, what is called, fan beams, may be used. In the case where the radiation source which emits fan beams is used, radiation is emitted from the radiation source in such a way that fan beams spread in a certain direction.

The subject table 70 is, as shown in FIG. 1, disposed between the radiation source 61 and the radiation detector F placed on the imaging table 50, and supports the subject H in a standing position. The subject table 70 is provided with: a carry device 71 which carries the subject table 70 in the up-and-down direction; and a support part 72, and moves (goes up and down) with the carry device 71 in synchronization with the fitting-part support part 54 of the imaging table 50 according to an instruction from the control box 80. The subject table 70 is made of a resin board such as an acrylic plate, a board of an inorganic material such as a carbon plate, a metal plate or the like.

The carry device 71 includes, for example, a driving motor (not shown), and transmits rotary force of the driving motor to the subject table 70 with a rack-and-pinion so as to move (go up and down) the subject table 70 in the up-and-down direction. The carry device 71 may adopt any configuration, mechanism or the like as long as it can move the subject table 70 in the up-and-down direction, and therefore is not limited to the configuration using the rack-and-pinion. For example, the carry device 71 may transmit linear movement of an actuator or the like to the subject table 70 so as to move the subject table 70. The same applies to the carry device 53.

The thus-configured tomography device 1 performs tomosynthesis imaging a predetermined number of times while moving the subject table 70 supporting the subject H and the imaging table 50 with the radiation detector F placed therein from their predetermined start positions to their predetermined end positions (in the up direction or the down direction) in synchronization with each other according to control signals sent from the console 90 through the control box 80 described below. Thus, the radiation detector F obtains a projection image (for each tomogram) each time tomosynthesis imaging is performed.

It is possible that while radiation is not intermittently but continuously emitted from the radiation source 61, the radiation detector F obtains a projection image (for each tomogram) (projection image obtaining processing) a predetermined number of times. Alternatively, it is possible that radiation is emitted from the radiation source 61 a predetermined number of times (pulse irradiation), and the radiation detector F obtains a projection image (for each tomogram) each time radiation is emitted from the radiation source 61.

The radiation detector F may send an obtained projection image to the console 90 as an image processing device through the control box 80 each time obtaining the projection image. Alternatively, the radiation detector F may temporarily store each obtained projection image in a storage unit (not shown), and send the projection images to the console 90 all together when completing the projection image obtaining processing a predetermined number of times.

In order to perform the projection image obtaining processing a predetermined number of times while moving the subject H from the start position to the end position, for example, the carry device 53 and the carry device 71 can appropriately determine a speed to move the fitting-part support part 54 and a speed to move the subject table 70, respectively.

For reconstruction described below, relative position information on the radiation source 61 and the subject H is needed. For that, a unit to detect a position of the subject table 70 may be provided to obtain position information on the subject table 70, or the subject table 70 may be configured to move within a predetermined area at a predetermined speed to have preset position information on the subject table 70. Then, the relative position information on the radiation source 61, which is fixed, and the subject H can be obtained from the position information on the subject table 70. Similarity, relative position information on the radiation source 61 and the radiation detector F is needed. For that, a unit to detect a position of the radiation detector F may be provided to obtain position information on the radiation detector F, or the radiation detector F may be configured to move within a predetermined area at a predetermined speed to have preset position information on the radiation detector F. Then, the relative position information on the fixed radiation source 61 and the radiation detector F can be obtained from the position information on the radiation detector F.

In the case where radiation is emitted from the radiation source 61 a predetermined number of time as described above, a speed at which the carry device 71 moves the subject table 70 (a speed at which the carry device 53 moves the imaging table 50), timing at which the irradiation device 60 makes the radiation source 61 emit radiation (irradiation interval) and the like are appropriately adjusted and determined.

The control box (also called a relay device or the like) 80 is connected with the components of the tomography device 1, the radiation detector F fitted in the fitting part 51, the console 90 and the like via the network N1. The control box 80 has a built-in convertor (not shown) which converts, for example, signals for LAN (Local Area Network) communication transmitted from the console 90 and the like to the irradiation device 60 into, for example, signals for the irradiation device 60, and vice versa.

Figure 2:
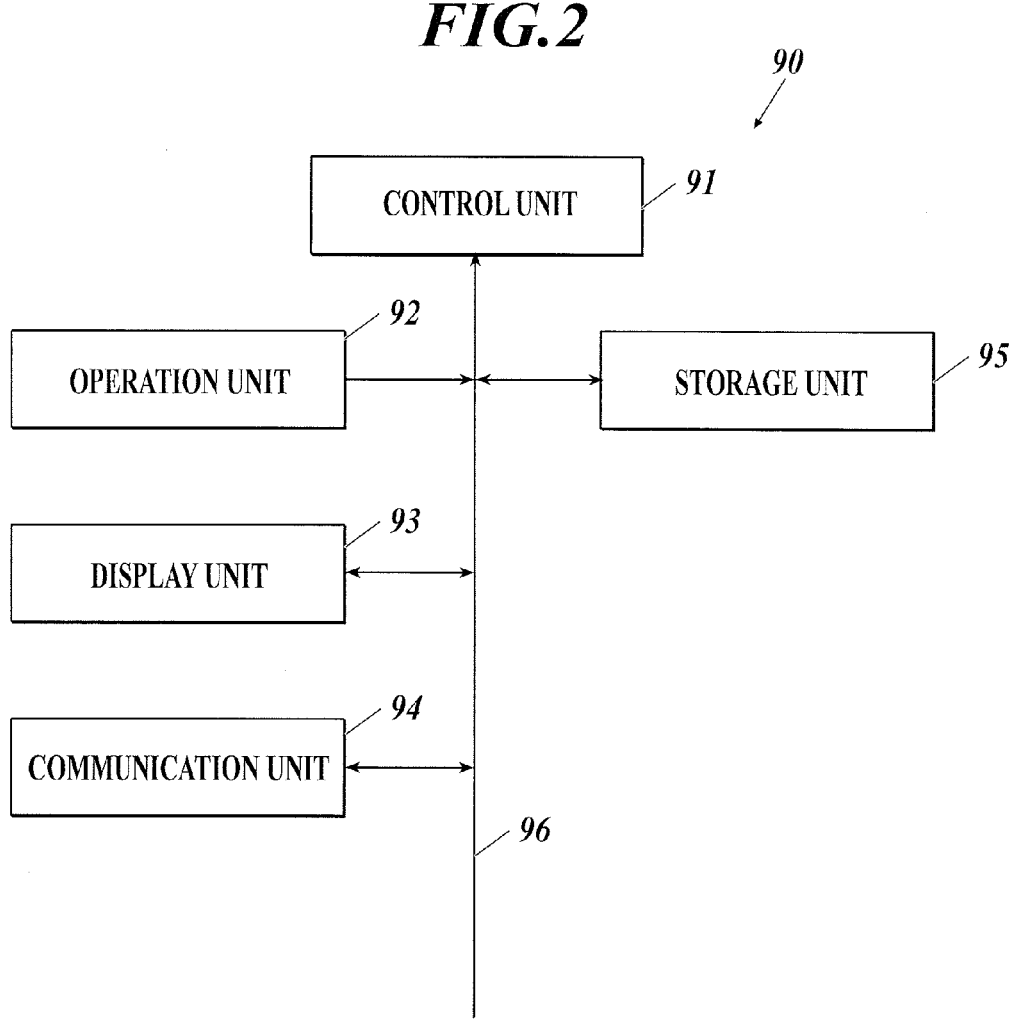
FIG. 2 is a block diagram showing the functional configuration of a console shown in FIG. 1.

The console 90 is a computer which includes, as shown in FIG. 2, a control unit 91, an operation unit 92, a display unit 93, a communication unit 94 and a storage unit 95 which are connected with each other via a bus 96.

The control unit 91 includes a CPU, a RAM and the like. The CPU of the control unit 91 reads various programs such as a system program and processing programs stored in the storage unit 95, opens the read programs on the RAM and performs various types of processing according to the opened programs. The control unit 91 functions as a reconstruction unit by working together with the programs stored in the storage unit 95.

The operation unit 92 includes: a keyboard including letter input keys, number input keys and various function keys; and a pointing device such as a mouse, and outputs press signals of keys pressed on the keyboard and operation signals made with the mouse to the control unit 91 as input signals.

The display unit 93 is constituted of, for example, a monitor such as a CRT (Cathode Ray Tube) or an LCD (Liquid Crystal Display), and displays various screens according to instructions of display signals input from the control unit 91.

The communication unit 94 is constituted of a LAN card or the like, and sends/receives data to/from external devices connected to the networks N1 and N2 through a switching hub.

The storage unit 95 is constituted of, for example, an HHD (Hard Disk Drive) or a semiconductor nonvolatile memory. The storage unit 95 stores therein the system program and various processing programs as described above.

The console 90 can, for example: control the radiation detector F, for example, by sending, with the communication unit 94, an awaking signal to the radiation detector F through the access point AP or the control box 80 so that the radiation detector F can change its state from a sleep state to a wake-up state; send a tube current and the like set by a photographer such as a radiologist using the operation unit 92 to the irradiation device 60 through the control box 80 so that the tube current and the like can be set to the irradiation device 60; and control the carry device 53 and the carry device 71 through the control box 80.

In the embodiment, the console 90 also functions as an image processing device as mentioned above, and when receiving projection images obtained by the radiation detector F from the tomography device 1 as described below, performs reconstructed image generation processing described below to reconstruct the projection images, thereby generating a two-dimensional tomogram of the subject. The image processing device may be a separate device from the console 90.

Further, as shown in FIG. 1, the console 90 is connected to the access point AP via the network N2. The console 90 is connected with an HIS (Hospital Information System), an RIS (Radiology Information System), a PACS (Picture Archiving and Communication System) and the like, all not shown, via the network N2. The console 90 performs various types of processing. Examples thereof include acquiring imaging order information necessary for imaging from the RIS and sending generated tomograms to the PACS.

In the case of the tomography system 100 shown in FIG. 1, the subject table 70, the carry device 71, the control box 80 and the like are introduced into a facility such as a hospital where the imaging table 50 and the irradiation device 60 are already introduced and the console 90 is connected to the HIS, the RIS, the PACS and the like via the network N2, and connected with the imaging table 50, the irradiation device 60, the console 90 and the like, which are already installed, via the network N1, thereby constituting the tomography system 100.

However, the network to connect these devices and the like is not necessary to be a plurality of networks such as the networks N1 and N2 in the embodiment, and the devices and the like may be connected to one network so as to constitute the tomography system 100. In the case where a plurality of networks are used as the network to connect the devices and the like as with the embodiment, which of the devices and the like is connected to which of the networks can be appropriately determined.

[Action of Tomography System 100]

Next, action of the tomography system 100 in the embodiment is described.

As shown in FIG. 3, intensities of radiation emitted from the radiation source 61 are not uniform by the heel effect, and the radiation intensity is lower at a large cone angle than at a small cone angle (see the lower graph in FIG. 3). Hence, intensities of the radiation reaching multiple points on the incidence face of the radiation detector F are not uniform either (see the upper graph in FIG. 3), and a density non-uniformity occurs in a projection image. Further, as described above, in the tomography system 100, in order to obtain projection images to generate a tomogram of the subject H, imaging is performed multiple times while the radiation detector F is moved in relation to the radiation source 61. During the time, when the radiation detector F is at a position far from the radiation source 61 (for example, around the start position or the end position of the movement of the radiation detector F), as shown in FIG. 3, the radiation is blocked by the collimator 75, so that there is generated an area (A1 or A2 in FIG. 3) where only a small amount of radiation reaches, and an area (vignetting portion) having a small signal value (density) exists in an obtained projection image because of the collimator 75. If a tomogram is generated by reconstruction based on the projection images having density non-uniformities caused by these, the generated tomogram has a large number of artifacts, which is unsuitable for a diagnosis. The artifact generated by vignetting which is caused by a collimator blocking radiation ("mechanical vignetting" or simply "vignetting") is unexpected in a conventional plain radiograph, which is obtained in such a way that the area of interest of a subject is imaged to be in the irradiation area.

Therefore, in the tomography system 100 in the first embodiment, each subject-included projection image is corrected on the basis of a profile of a corresponding no-subject-included projection image (profile of signal values of pixels thereof), and a reconstructed image is generated on the basis of the corrected subject-included projection images.

More specifically, first, in the tomography device 1, imaging is performed a predetermined number of times while the radiation detector F is moved in relation to the radiation source 61 in a state in which no subject H is on the subject table 70, whereby a series of no-subject-included projection images are generated and sent to the console 90. Next, in the tomography device 1, imaging is performed a predetermined number of times while the radiation detector F and the subject table 70 are moved in relation to the radiation source 61 in a state in which a subject H is on the subject table 70, whereby a series of subject-included projection images are generated and sent to the console 90.

The imaging to obtain no-subject-included projection images is performed before the imaging to obtain subject-included projection images in the embodiment, but may be performed after the imaging to obtain subject-included projection images.

When receiving the projection images via the communication unit 94, the control unit 91 of the console 90 performs reconstructed image generation processing A on the basis of the received projection images.

FIG. 4 is a flowchart of the reconstructed image generation processing A performed by the control unit 91. The reconstructed image generation processing A is performed by the control unit 91 working together with the programs stored in the storage unit 95.

First, the control unit 91 creates a profile in a moving direction of the radiation detector F in a no-subject-included projection image (Step S1).

The moving direction of the radiation detector F in a projection image is a direction in which pixels of the projection image are arranged, the pixels corresponding to detection elements of the radiation detector F arranged along the moving direction of the radiation detector F. Hereinafter, this direction in a projection image is referred to as a column direction, and a direction at right angles to the column direction is referred to as a row direction.

At Step S1, the control unit 91 creates the profile in the moving direction (column direction) of the radiation detector F, for example, by calculating an average value of signal values in the row direction for each row of the no-subject-included projection image.

FIG. 5 shows a no-subject-included projection image and a profile in the moving direction (column direction) of the radiation detector F in the no-subject-included projection image. In FIG. 5, as an example, a profile of a no-subject-included projection image containing a vignetting portion is shown.

In a no-subject-included projection image, the signal value of a pixel of a portion formed without radiation attenuation indicates the maximum signal value whereas the signal value of a pixel of a portion formed with radiation attenuation by the heel effect and/or the collimator 75 becomes smaller according to how much radiation is attenuated. In particular, in the case where radiation is blocked by the collimator 75, because only a small amount of radiation reaches a point on the radiation detector F, vignetting occurs in a portion of a no-subject-included projection image corresponding to the point, and when a profile in the moving direction of the radiation detector F in the no-subject-included projection image is obtained, as shown in FIG. 5, the obtained profile indicates that the signal value significantly decreases at a border B between a vignetting portion and a no-vignetting portion.

Next, the control unit 91 calculates correction values for a corresponding subject-included projection image on the basis of the created profile (Step S2). For example, the maximum value of the created profile and the value of each row of the profile are compared with each other so that a ratio (value of the profile/maximum value of the profile) is calculated for each row, and on the basis of the calculated ratio, for example, a reciprocal of the ratio is calculated as a correction value for each corresponding row of the subject-included projection image.

Next, the control unit 91 corrects the subject-included projection image on the basis of the calculated correction values (Step S3). That is, the signal value of each pixel of the subject-included projection image is multiplied by the correction value calculated for the row to which the pixel belongs. Qualities of the radiation (X ray) to the subject-included projection image and the no-subject-included projection image may be different, and therefore the subject-included projection image may not be accurately corrected with the correction values as they are. Hence, the difference in radiation quality between the subject-included projection image and the no-subject-included projection image may be experimentally acquired by imaging a phantom and incorporated into the correction values.

Steps S1 to S3 (i.e. correction processing) are performed with respect to each of the received subject-included projection images and their corresponding no-subject-included projection images.

Next, the control unit 91 generates a reconstructed image (tomogram) of the subject H on the basis of the corrected subject-included projection images (Step S4). To generate a reconstructed image, a well-known method can be used. Examples thereof include: analytical image reconstruction methods such as the Feldkamp method and the shift-and-add method; and the successive approximation image reconstruction method.

Thus, a reconstructed image in which artifacts are minimized can be obtained by generating the reconstructed image on the basis of the subject-included projection images, which have been corrected to correct density non-uniformities therein caused by vignetting and the heel effect.

Second Embodiment

Next, a second embodiment of the present invention is described.

The configuration of the tomography system 100 in the second embodiment is the same as that thereof described in the first embodiment, and therefore description thereof is omitted here, and action thereof in the second embodiment is described hereinafter.

In the second embodiment, first, in the tomography device 1, imaging is performed a predetermined number of times while the radiation detector F and the subject table 70 are moved in relation to the radiation source 61 in a state in which a subject H is on the subject table 70, whereby a series of subject-included projection images are generated and sent to the console 90.

When receiving the projection images via the communication unit 94, the control unit 91 of the console 90 performs reconstructed image generation processing B on the basis of the received projection images.

FIG. 6 is a flowchart of the reconstructed image generation processing B performed by the control unit 91. The reconstructed image generation processing B is performed by the control unit 91 working together with the programs stored in the storage unit 95.

First, the control unit 91 creates a profile in the moving direction (column direction) of the radiation detector F in a subject-included projection image (Step S11). The control unit 91 creates the profile in the moving direction (column direction) of the radiation detector F, for example, by calculating an average value of signal values in the row direction for each row of the subject-included projection image.

FIG. 7 shows a subject-included projection image and a profile in the moving direction (column direction) of the radiation detector F in the subject-included projection image as an example. In FIG. 7, as an example, a profile of a subject-included projection image containing a vignetting portion with a subject all over the image is shown.

In a subject-included projection image, the signal values of pixels are affected by both radiation attenuation by the heel effect and/or the collimator 75 and radiation attenuation by radiation absorption with a structure of the subject H. The difference in the amount of radiation between a direct exposure portion formed by radiation directly reaching the radiation detector F and a bone portion formed by radiation reaching the radiation detector F through a bone of a human body, the bone greatly absorbing radiation, is expressed as about $\frac{1}{10}$ (bone portion/direct exposure portion) whereas the difference in the amount of radiation between a direct exposure portion and a vignetting portion is expressed as $\frac{1}{20}$ (vignetting portion/direct exposure portion) or less. The difference in the latter is much larger than the difference in the former. Hence, as shown in FIG. 7, the profile of the subject-included projection image too indicates that the signal value significantly decreases at a border B between a vignetting portion and a no-vignetting portion.

Next, the control unit 91 calculates correction values for the subject-included projection image on the basis of the created profile (Step S12). For example, a point at which a difference (ratio) between values of pixels adjacent to each other in the column direction in the created profile is more than a predetermined threshold value is detected as the border B between the vignetting portion and the no-vignetting portion, and the low signal side of the border B is recognized as the vignetting portion. Then, the profile of the vignetting portion is smoothed because fluctuation (see FIG. 7), which is caused by the subject H, in the vignetting portion in the created profile may badly affect the corrected subject-included projection image (and, by extension, be bad influence on a reconstructed image to be generated). Then, the maximum value of the created profile (or average value of values of the no-vignetting portion in the profile) and the value of each row of the vignetting portion in the profile are compared with each other so that a ratio (value of the profile/maximum value of the profile (or average value of values of the no-vignetting portion in the profile)) is calculated for each row of the vignetting portion, and on the basis of the calculated ratio, for example, a reciprocal of the ratio is calculated as a correction value for each row of the vignetting portion of the subject-included projection image. The correction values for the no-vignetting portion are 1.

Next, the control unit 91 corrects the subject-included projection image on the basis of the calculated correction values (Step S13). That is, the signal value of each pixel of the subject-included projection image is multiplied by the correction value calculated for the row to which the pixel belongs. With regard to the no-vignetting portion, multiplication of the signal value of each pixel by its correction value may be omitted.

Steps S11 to S13 (i.e. correction processing) are performed with respect to each of the received subject-included projection images.

Next, the control unit 91 generates a reconstructed image (tomogram) on the basis of the corrected subject-included projection images (Step S14). To generate a reconstructed image, a well-known method can be used. Examples thereof include: analytical image reconstruction methods such as the Feldkamp method and the shift-and-add method; and the successive approximation image reconstruction method.

Thus, a reconstructed image in which artifacts are minimized can be obtained by generating the reconstructed image on the basis of the subject-included projection images, which have been corrected to correct density non-uniformities caused by vignetting and the heel effect.

<Modifications>

The profile created at Step S11 may be created as follows.

For example, in the case where a site of a subject is small to the radiation detector F, and as shown in FIG. 8, a direct exposure portion R along the moving direction of the radiation detector F exists in a subject-included projection image, a profile of the direct exposure portion R may be created, for example, by calculating an average value of signal values in the row direction for each row of the direct exposure portion R. Then, at Step S12, correction values may be calculated on the basis of the profile created on the basis of the direct exposure portion R. More specifically, the maximum value of the created profile and the value of each row of the profile are compared with each other so that a ratio (value of the profile/maximum value of the profile) is calculated for each row, and on the basis of the calculated ratio, for example, a reciprocal of the ratio is calculated as a correction value for each row of the subject-included projection image. Then, at Step S13, the signal value of each pixel of the subject-included projection image may be multiplied by the correction value calculated for the row to which the pixel belongs, whereby the subject-included projection image is corrected. In this way, without taking no-subject-included projection images, subject-included projection images can be corrected to correct density non-uniformities caused by vignetting and the heel effect, whereby corrected subjected-included projection images can be generated, and a reconstructed image in which artifacts are minimized can be obtained by generating the reconstructed image on the basis of the corrected subject-included projection images.

Further, for example, in the case where, as shown in FIG. 9, direct exposure portions R1 and R2 along the moving direction of the radiation detector F exist on both sides in a subject-included projection image, a profile of each of the direct exposure portions R1 and R2 may be created. Then, at Step S12, on the basis of the profiles of the direct exposure portions R1 and R2, for example, profiles of columns between the direct exposure portions R1 and R2 may be interpolated so that the profiles of the columns of the subject-included projection image can be created, and on the basis of the created and interpolated profiles, correction values for pixels of the subject-included projection image may be calculated.

For example, for each row, as shown in FIG. 9, values of the profiles of the direct exposure portions R1 and R2 are plotted, and a linear approximation is performed on the plotted points, whereby the profiles of the columns between the direct exposure portions R1 and R2 are interpolated. Then, the maximum value of the profile created for each column and the value of each row of the profile are compared with each other so that a ratio (value of the profile/ maximum value of the profile) is calculated for each row, and on the basis of the calculated ratio, for example, a reciprocal of the ratio is calculated as a correction value for each row of the column (i.e. a correction value for each pixel of the column) of the projection image. In this way, when a density non-uniformity exists in the row direction of a subject-included projection image, that non-uniformity can also be corrected, and therefore correction accuracy can be further increased.

In FIGS. 8 and 9, the direct exposure portions R, R1 and R2 are shown as belt-shaped areas in white, but in reality, signal values exist in the direct exposure portions R, R1 and R2 too.

The direct exposure portions R, R1 and R2 may be determined on the basis of information on a site of a subject included in the imaging order information for projection images. Alternatively, a user may specify a direct exposure portion by operating the operation unit 92 with a projection image displayed on the display unit 93.

Third Embodiment

Next, a third embodiment of the present invention is described.

The configuration of the tomography system 100 in the third embodiment is the same as that thereof described in the first embodiment, and therefore description thereof is omitted here, and action thereof in the third embodiment is described hereinafter.

In the tomography system 100 in the third embodiment, a reconstructed image is generated with the successive approximation image reconstruction method. For that, the console 90 performs reconstructed image generation processing C, thereby creating a profile of each no-subject-included projection image or each subject-included projection image sent from the tomography device 1; correcting, on the basis of the created profile, a detection probability (detection probabilities) used in image reconstruction with the successive approximation image reconstruction method; and generating a tomogram, which is a reconstructed image, with the successive approximation image reconstruction method on the basis of the corrected detection probabilities.

Figure 10:
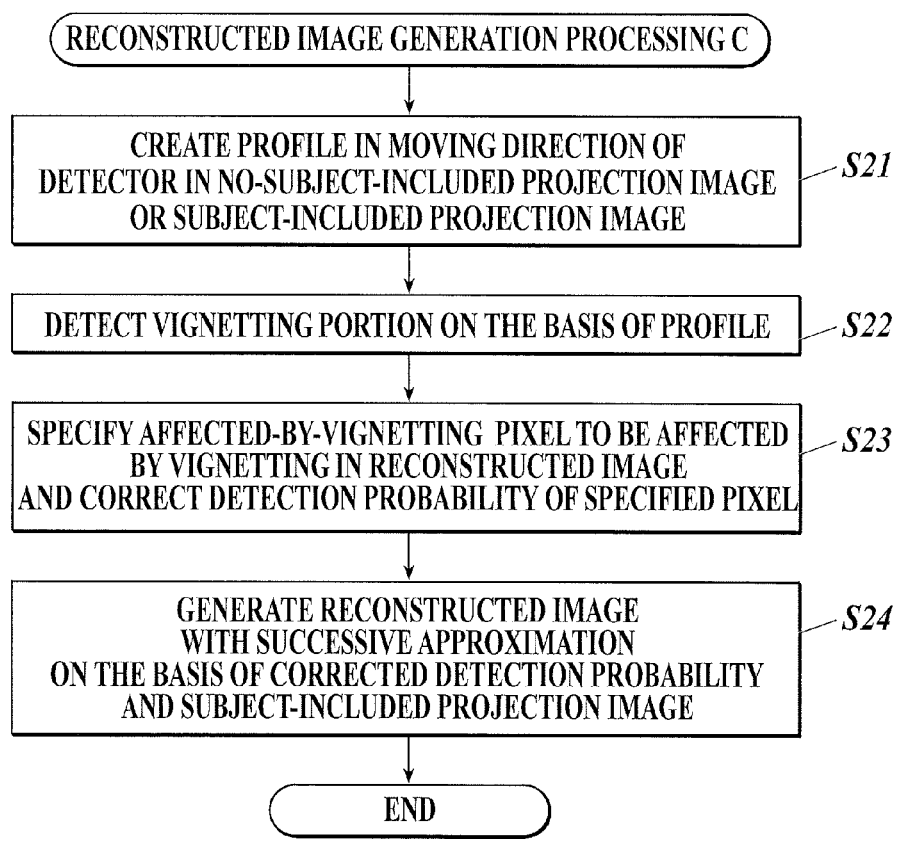
FIG. 10 is a flowchart of reconstructed image generation processing C performed by the control unit shown in FIG. 2 in a third embodiment.

FIG. 10 is a flowchart of the reconstructed image generation processing C performed by the control unit 91. The reconstructed image generation processing C is performed by the control unit 91 working together with the programs stored in the storage unit 95.

First, the control unit 91 creates a profile in the moving direction of the radiation detector F in a no-subject-included projection image or a subject-included projection image (Step S21).

The method for creating the profile is the same as that described in the first and second embodiments, and therefore description thereof is omitted here.

Next, the control unit 91 detects a vignetting portion in the projection image on the basis of the created profile (Step S22).

At Step S22, for example, a point (row) at which a difference (ratio) between values of pixels adjacent to each other in the column direction in the created profile is more than a predetermined threshold value is detected as a border B between a vignetting portion and a no-vignetting portion, and the low signal side of the border B is detected as the vignetting portion.

Next, when detecting the vignetting portion, the control unit 91 specifies a pixel(s) to be affected by vignetting (affected-by-vignetting pixel(s)) in a reconstructed image on the basis of the position of the detected vignetting portion in the projection image, and corrects a detection probability (detection probabilities) of the specified pixel (Step S23).

The successive approximation image reconstruction method is a well-known reconstructed image generation method as described, for example, in Reference Document 1 (Reference Document 1: Hiroyuki SHINOHARA, Kazuma NAKASEKO, Kazuya SAKAGUCHI and Takeyuki HASHIMOTO, *Gazou Saikousei Shirizu, Chikuji Kinji Gazou Saikousei no Kiso* (*Image Reconstruction Series, Basis of Successive Approximation Image Reconstruction*), IRYO KAGAKU-SYA Inc., 2013). The successive approximation image reconstruction method is, in general, a method of: making an optical model (detection probability, etc.), a statistical model or the like; according to the model, on a calculator, comparing a projection image (called an assumed projection image) generated by projecting a working reconstructed image with a projection image actually taken; and back-projecting the comparison result so as to successively update the reconstructed image with the obtained value as a feedback value, thereby making the reconstructed image approximate to a true reconstructed image. Examples of the successive approximation image reconstruction method using the detection probability include ML-EM (Maximum Likelihood-Expectation Maximization) and SART. In the embodiment, ML-EM is described as an example. Pixels and detectors are represented by one-dimensional variables in the following description.

Figure 11:
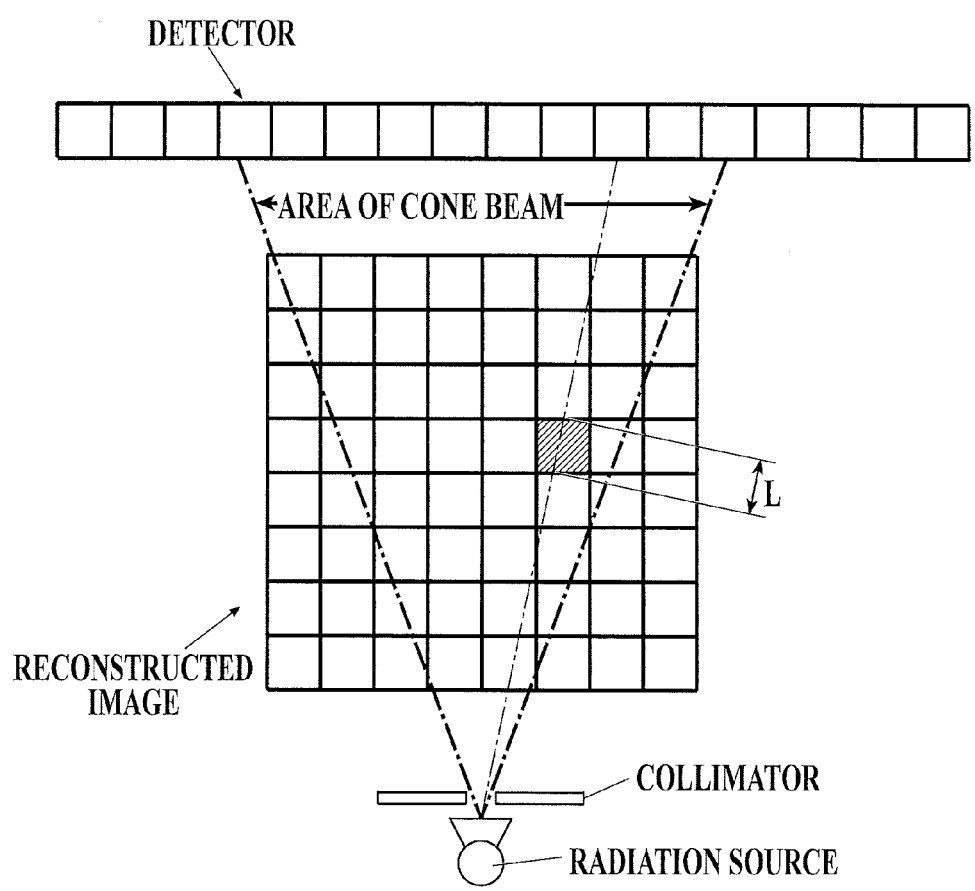
FIG. 11 is an illustration to explain an example of how to calculate a detection probability used in the successive approximation image reconstruction method.

A detection probability $C_{ij}$ is a rate with which the $j^{th}$ pixel (pixel j) in a reconstructed image affects the $i^{th}$ detector (detector (detection element) i). The detection probability $C_{ij}$ is determined by geometric arrangement of the pixel j and the detector i. Into the detection probability $C_{ij}$, physical phenomena such as defocus and photon scatter may be incorporated. As a method for calculating the detection probability $C_{ij}$, there are various proposals. For example, as shown in FIG. 11, assuming that there is a projection line (a thin dashed line in FIG. 11) which connects the focus of a radiation source and the center of a detector when actual projection images in multiple directions are collected for a reconstructed image, the detection probability $C_{ij}$ can be obtained on the basis of the length of a line segment L of the projection line which connects the focus of the radiation source and the center of the detector i, the line segment L crossing the pixel j. Alternatively, the area of a portion where the projection line having a width of one pixel and the pixel j cross may be used as the detection probability $C_{ij}$. The detection probability $C_{ij}$ is calculated in advance for each of all combinations of pixels and detectors.

In ML-EM, using the detection probability $C_{ij}$, the k+1$^{th}$ reconstructed image is generated from the k$^{th}$ reconstructed image through the following (1) to (4). Note that "k" represents the number of updates; "j" represents a pixel number of a reconstructed image, and "J" represents the total number of pixels; "i" represents a detector (detection element) number, and "I" represents the total number of detectors; $C_{ij}$ represents a detection probability; "$\lambda_j^{(k)}$" and "$\lambda_j^{(k+1)}$" represent pixel values of reconstructed images generated the k$^{th}$ time and the k+1$^{th}$ time, respectively; and $y_i$ represents a value of a projection image (actual projection image) actually taken.

(1) First, with the following Formula 1 using a detection probability $C_{ij}$, the k$^{th}$ assumed projection image $y_i^{(k)}$ is generated by projecting the k$^{th}$ reconstructed image $\lambda_j^{(k)}$.

$$y_i^k = \sum_{m=1}^{J} C_{im} \lambda_m^k \qquad \text{[Formula 1]}$$

(2) Next, with the following Formula 2, a ratio $y_i'$ of an actual projection image $y_i$ to the k$^{th}$ assumed projection image $y_i^{(k)}$ is calculated.

$$y_i' = \frac{y_i}{y_i^k} \qquad \text{[Formula 2]}$$

(3) Next, with the following Formula 3 using the detection probability $C_{ij}$, a feedback value $\lambda_j'$ is calculated by back-projecting the calculated ratio $y_i'$.

$$\lambda_j' = \frac{1}{\sum_{i=1}^{I} C_{ij}} \sum_{i=1}^{I} y_i' C_{ij} \qquad \text{[Formula 3]}$$

(4) Next, with the following Formula 4, the k+1th reconstructed image $\lambda_j(k+1)$ is generated by multiplying the k$^{th}$ reconstructed image $\lambda_j^{(k)}$ by the feedback value $\lambda_j'$.

$$\lambda_j^{k+1} = \lambda_j^k \cdot \lambda_j' \qquad \text{[Formula 4]}$$

The above (1) to (4) are repeated until a certain condition is satisfied. Examples of the condition include a condition that a predetermined number of updates is reached, and a condition that the difference between the assumed projection image $y_i^{(k)}$ and the actual projection image $y_i$ becomes a predetermined threshold value or less. The reconstructed image of the time when the repeat ends is taken as an assumed reconstructed image.

If vignetting, which is caused by a collimator, is not taken into account in the detection probability, and a projection image which has not been corrected to correct a density non-uniformity caused by vignetting is taken as an actual projection image, in comparison of the actual projection image with an assumed projection image generated on a calculator (the above (2)), the density non-uniformity occurs in an area in the ratio (i.e. in a difference image), the area corresponding a vignetting portion of the actual projection image. In the successive approximation image reconstruction method, a working reconstructed image is updated by feedback of the comparison result which, in the above case, includes that density non-uniformity. Therefore, an artifact generated by the density non-uniformity appears in a reconstructed image to be generated. On the other hand, when the detection probability of an affected-by-vignetting pixel is corrected to the detection probability in which influence of vignetting is taken into account as with the embodiment, in comparison of an actual projection image with an assumed projection image generated on a calculator, the density non-uniformity caused by vignetting can be minimized. Further, by updating a working reconstructed image multiple times with a feedback value based on the comparison result which includes the minimized density non-uniformity caused by vignetting, an artifact generated thereby in a reconstructed image to be generated can also be minimized.

Figure 12:
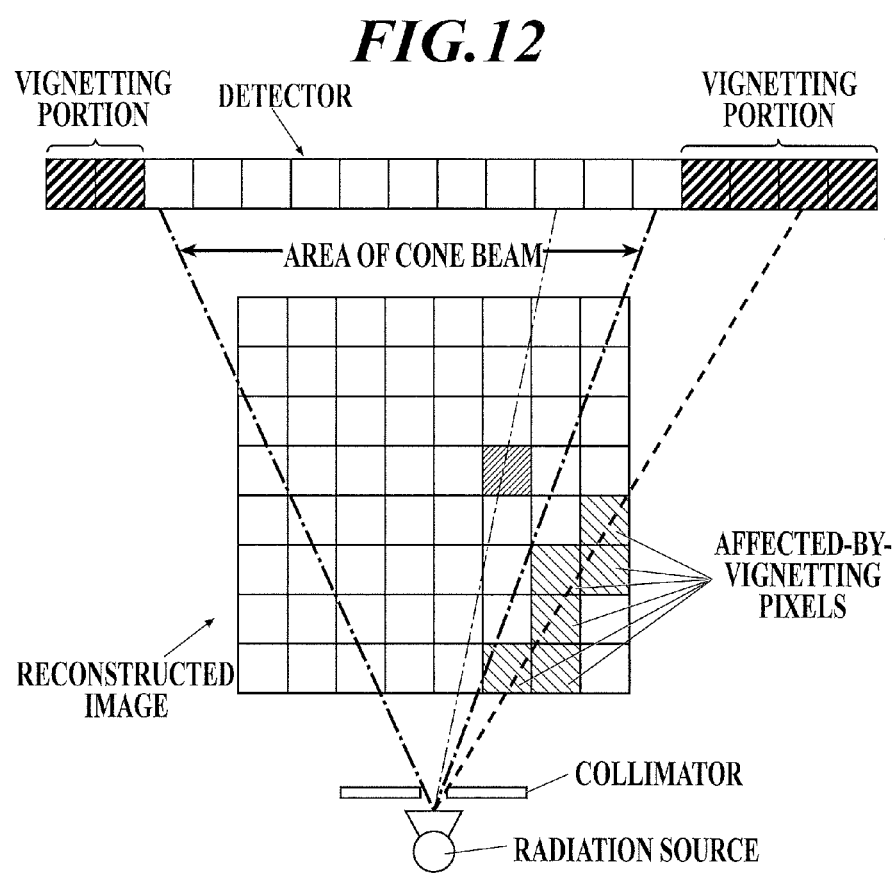
FIG. 12 is an illustration to explain affected-by-vignetting pixels.

At Step S23, for example, as shown in FIG. 12, the control unit 91 specifies, on the basis of the position of the vignetting portion in the projection image detected at Step S22, the pixel(s) to be affected by vignetting (affected-by-vignetting pixel(s)) in the reconstructed image, and corrects the detection probability of the specified affected-by-vignetting pixel to 0 or to the detection probability according to the radiation intensity (signal value) of the vignetting portion. For example, the maximum value of the profile created at Step S21 and the value of each row of the vignetting portion in the created profile are compared with each other so that a ratio (value of the profile/maximum value of the profile) is calculated, and the detection probability obtained in advance with regard to the affected-by-vignetting pixel is multiplied by the calculated ratio, whereby the detection probability is corrected.

Steps S21 to S23 (i.e. correction processing) are performed with respect to each of the received subject-included projection images and, if any, their corresponding no-subject-included projection images.

When finishing correcting the detection probabilities, the control unit 91 generates the reconstructed image (tomogram) with the successive approximation image reconstruction method described above on the basis of the corrected detection probabilities and the subject-included projection images obtained by imaging (Step S24).

Thus, a reconstructed image in which an artifact generated by vignetting is minimized can be obtained by correcting the detection probabilities in advance according to radiation attenuation caused by the collimator 75, and generating the reconstructed image using the corrected detection probabilities.

The vignetting portion is considered to have much noise because the portion is hardly irradiated. Hence, in the first to third embodiments, it is preferable that, when detecting a vignetting portion from a profile in the moving direction of the radiation detector F in a projection image, the control unit 91 perform the correction processing (Steps S1 to S3 in FIG. 4, Steps S11 to S13 in FIG. 6, or Steps S21 to S23 in FIG. 10) and the restricted-image generation after performing smoothing processing on the vignetting portion. A reconstructed image in which an artifact generated by noise is minimized can be obtained by performing the correction processing on subject-included projection images and the reconstruction based on the corrected subject-included projection images after performing the smoothing processing on the detected vignetting portion(s). Examples of the smoothing processing include filtering processing on a projection image using a spatial frequency filter such as a mean filter, a Gaussian filter or a median filter.

As described above, the tomography system 100 in the first embodiment (i) creates a profile of pixel signal values from each no-subject-included projection image obtained by tomosynthesis imaging without a subject H on the subject table 70 in the tomography device 1, (ii) corrects, on the basis of the created profile, each corresponding subject-included projection image obtained by tomosynthesis imaging with a subject H on the subject table 70 in the tomography device 1 and (iii) generates a reconstructed image on the basis of the corrected subject-included projection images.

Consequently, a tomogram, which is a reconstructed image, is generated using the subject-included projection images, which have been corrected to minimize density non-uniformities caused by the heel effect, vignetting and the like, and therefore a reconstructed image in which artifacts are minimized can be obtained.

Further, the console 90 of the tomography system 100 in the second embodiment (i) creates a profile of pixel signal values from each subject-included projection image obtained by tomosynthesis imaging with a subject H on the subject table 70 in the tomography device 1, (ii) corrects the subject-included projection image on the basis of the created profile and (iii) generates a reconstructed image on the basis of the corrected projection images.

Consequently, a tomogram, which is a reconstructed image, is generated using the subject-included projection images, which have been corrected to minimize density non-uniformities caused by the heel effect, vignetting and the like, and therefore a reconstructed image in which artifacts are minimized can be obtained. In addition, the subject-included projection images are corrected on the basis of the profiles created from the subject-included projection images. Consequently, the subject-included projection images can be corrected without taking no-subject-included projection images.

For example, in the case where a direct exposure portion along the moving direction of the radiation source 61 or the radiation detector F exists in a subject-included projection image, the console 90 creates a profile of pixel signal values of the direct exposure portion and corrects the subject-included projection image on the basis of the created profile. Consequently, a tomogram, which is a reconstructed image, is generated using the subject-included projection images, which have been corrected to minimize density non-uniformities caused by the heel effect, vignetting and the like, and therefore a reconstructed image in which artifacts are minimized can be obtained. Further, in the case where direct exposure portions along the moving direction of the radiation source 61 or the radiation detector F exist on both sides in a subject-included projection image, the console 90 (i) creates a profile of pixel signal values of each of the direct exposure portions, (ii) interpolates a profile(s) between the direct exposure portions on the basis of the created profile and (iii) corrects the subject-included projection image on the basis of the created profiles and the interpolated profile. Consequently, each subject-included projection image can be corrected with high accuracy when a density non-uniformity exists in the row direction of the subject-included projection image.

Further, the console 90 (i) creates a profile(s) in the moving direction of the radiation source 61 or the radiation detector F in a projection image, (ii) detects, on the basis of the created profile, a vignetting portion where vignetting occurs by radiation blocked by the collimator 75 and (iii) corrects influence of the radiation attenuation in the vignetting portion detected in the projection image on a tomogram to be generated. Consequently, a tomogram, which is a reconstructed image, is generated using the subject-included projection images, which have been corrected to minimize density non-uniformities caused by vignetting and the like, and therefore a reconstructed image in which artifacts are minimized can be obtained.

Further, the console 90 performs the correction processing and the reconstruction using the corrected subject-included projection images after performing the smoothing processing on the vignetting portions. Consequently, a reconstructed image in which an artifact generated by noise is minimized can be obtained.

Further, in the case where a tomogram, which is a reconstructed image, is generated with the successive approximation image reconstruction method, the console 90 corrects detection probabilities instead of subject-included projection images, and reconstructs subject-included projection images using the corrected detection probabilities. Consequently, as with the above, a reconstructed image in which artifacts are minimized can be obtained.

Thus, the present invention can minimize artifacts which appear in a tomogram when any of projection images obtained by imaging has density non-uniformity.

The above embodiments are preferred examples of the tomography system of the present invention, and therefore the present invention is not limited thereto.

For example, in the first embodiment and the modifications of the second embodiment, each row of each subject-included projection image is corrected without detecting a vignetting portion. However, as with the second embodiment, it is possible that a vignetting portion is detected on the basis of a profile(s), and the signal values of the detected vignetting portion is corrected.

Further, for example, in the embodiments, the radiation detector F is, what is called, a portable radiation detector (also called a cassette radiation detector or the like), and tomography is performed with the radiation detector F fitted in the fitting part 51 (shown in FIG. 1) of the imaging table 50 of the tomography device 1. However, the present invention is applicable not only to the portable radiation detector F but also to a radiation detector integrated with the imaging table 50, what is called, a specialized radiation detector.

Further, in the embodiments, the tomography device 1 is a device which performs imaging with a subject H in a standing position. However, the tomography device 1 may be a device which moves the radiation detector F and the subject H in the horizontal direction, thereby performing imaging with the subject H in a reclining position.

Further, in the embodiments, as a preferred example, the tomography device 1 has the fixed radiation source 61 and performs imaging while moving the radiation detector F and the subject H in the same way in relation to the radiation source 61. However, the tomography device 1 is not limited thereto as long as it performs tomosynthesis imaging. For example, the tomography device 1 may perform imaging while moving the radiation source 61 and the radiation detector F in directions opposite to each other. Alternatively, the tomography device 1 may have the radiation detector F which is fixed and move the radiation source 61. In this case, the moving direction of the radiation detector F described above is the moving direction of the radiation source 61. An imaging device which has the fixed radiation source 61 and moves the radiation detector F in relation to the fixed radiation source 61 as with the embodiments easily causes vignetting and the heel effect (see FIG. 3) in particular, and therefore the present invention is particularly suitable for a system which generates each tomogram from projection images taken by this sort of device.

Further, in the above, a hard disk, a semiconductor nonvolatile memory or the like is used as a computer readable storage medium of the programs of the present invention. However, this is not a limitation, and hence, for example, a portable storage medium such as a CD-ROM is also usable as the computer readable storage medium. Further, a carrier wave is usable as a medium to provide data of the programs of the present invention via a communication line.

The other specific configurations and actions of the devices and the like of the tomography system can also be appropriately modified without departing from the scope of the present invention.

This application is based upon and claims the benefit of priority under 35 USC 119 of Japanese Patent Application No. 2013-260756 filed on Dec. 18, 2013, the entire disclosure of which, including the specification, claims, drawings and abstract, is incorporated herein by reference in its entirety.

What is claimed is:

1. A tomography system comprising:
a radiation source which emits radiation to a subject;
a radiation detector (i) in which radiation detection elements are two-dimensionally disposed, the radiation detection elements detecting the radiation to generate electric signals, and (ii) which obtains a projection image according to the radiation;
a subject table which is disposed between the radiation source and the radiation detector and supports the subject;
an imaging unit which obtains the projection image a predetermined number of times while changing a positional relationship of the radiation source and the radiation detector; and
a reconstruction unit which generates a tomogram of the subject using the projection images obtained by the imaging unit, the reconstruction unit including:
a correction unit which performs correction processing to (i) create a profile of a pixel signal value from a no-subject-included projection image obtained by the imaging unit without the subject on the subject table and (ii) correct, on the basis of the created profile, a subject-included projection image obtained by the imaging unit with the subject on the subject table or a detection probability used in generating the tomogram of the subject.

2. The tomography system according to claim 1, wherein the correction unit performs the correction processing to (i) create the profile in a moving direction of the radiation source or the radiation detector in the no-subject-included projection image, (ii) detect, on the basis of the created profile, a vignetting portion in which vignetting occurs by the radiation blocked by a collimator and (iii) correct influence of attenuation of the radiation in the vignetting portion on the tomogram by correcting the subject-included projection image or the detection probability.

3. The tomography system according to claim 1, wherein the correction unit performs the correction processing after performing smoothing processing on a vignetting portion in which vignetting occurs by the radiation blocked by a collimator in the no-subject-included projection image.

4. The tomography system according to claim 1, wherein the radiation source is fixed, and
the tomography system further comprises a first carry device which moves the radiation detector in relation to the fixed radiation source.

5. The tomography system according to claim 4 further comprising a second carry device which moves the subject table in a direction the same as a moving direction of the radiation detector, wherein
the radiation detector and the subject table move in synchronization with each other in relation to the radiation source.

6. A tomography system comprising:
a radiation source which emits radiation to a subject;
a radiation detector (i) in which radiation detection elements are two-dimensionally disposed, the radiation detection elements detecting the radiation to generate electric signals, and (ii) which obtains a projection image according to the radiation;
a subject table which is disposed between the radiation source and the radiation detector and supports the subject;
an imaging unit which obtains the projection image a predetermined number of times while changing a positional relationship of the radiation source and the radiation detector; and
a reconstruction unit which generates a tomogram of the subject using the projection images obtained by the imaging unit, the reconstruction unit including:
a correction unit which performs correction processing to (i) create a profile of a pixel signal value from a subject-included projection image obtained by the imaging unit with the subject on the subject table and (ii) correct, on the basis of the created profile, the subject-included projection image or a detection probability used in generating the tomogram of the subject.

7. The tomography system according to claim 6, wherein when a direct exposure portion along a moving direction of the radiation source or the radiation detector exists in the subject-included projection image, the correction unit performs the correction processing to (i) create a profile of a pixel signal value of the direct exposure portion and (ii) correct the subject-included projection image or the detection probability on the basis of the created profile.

8. The tomography system according to claim 6, wherein when direct exposure portions along a moving direction of the radiation source or the radiation detector exist on both sides in the subject-included projection image, the correction unit performs the correction processing to (i) create a profile of a pixel signal value of each of the direct exposure portions, (ii) interpolate a profile between the direct exposure portions on the basis of the created profiles and (iii) correct the subject-included projection image or the detection probability on the basis of the created profiles and the interpolated profile.

9. The tomography system according to claim 6, wherein the correction unit performs the correction processing to (i) create the profile in a moving direction of the radiation source or the radiation detector in the subject-included projection image, (ii) detect, on the basis of the created profile, a vignetting portion in which vignetting occurs by the radiation blocked by a collimator and (iii) correct influence of attenuation of the radiation in the vignetting portion on the tomogram by correcting the subject-included projection image or the detection probability.

10. The tomography system according to claim 6, wherein the correction unit performs the correction processing after performing smoothing processing on a vignetting portion in which vignetting occurs by the radiation blocked by a collimator in the subject-included projection image.

11. The tomography system according to claim 6, wherein
the radiation source is fixed, and
the tomography system further comprises a first carry device which moves the radiation detector in relation to the fixed radiation source.

12. The tomography system according to claim 11 further comprising a second carry device which moves the subject table in a direction the same as a moving direction of the radiation detector, wherein
the radiation detector and the subject table move in synchronization with each other in relation to the radiation source.

* * * * *